(12) United States Patent
Felsenstein et al.

(10) Patent No.: US 12,145,962 B2
(45) Date of Patent: Nov. 19, 2024

(54) CONSTRUCTION AND METHODS OF USE OF A BARCODED AND GENE EDITED DNA LIBRARY

(71) Applicant: The Regents of the University of Colorado, a Body Corporate, Denver, CO (US)

(72) Inventors: Kenneth Felsenstein, Denver, CO (US); Dan Theodorescu, Englewood, CO (US); Ryan T. Gill, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 1060 days.

(21) Appl. No.: 16/966,339

(22) PCT Filed: Feb. 4, 2019

(86) PCT No.: PCT/US2019/016522
§ 371 (c)(1),
(2) Date: Jul. 30, 2020

(87) PCT Pub. No.: WO2019/152932
PCT Pub. Date: Aug. 8, 2019

(65) Prior Publication Data
US 2020/0370203 A1    Nov. 26, 2020

Related U.S. Application Data

(60) Provisional application No. 62/727,438, filed on Sep. 5, 2018, provisional application No. 62/647,589, filed on Mar. 23, 2018, provisional application No. 62/626,560, filed on Feb. 5, 2018.

(51) Int. Cl.
*C07H 21/02* (2006.01)
*C12N 9/22* (2006.01)
*C12N 15/64* (2006.01)
*C40B 50/06* (2006.01)
*C40B 40/08* (2006.01)

(52) U.S. Cl.
CPC .............. *C07H 21/02* (2013.01); *C12N 9/22* (2013.01); *C12N 15/64* (2013.01); *C40B 50/06* (2013.01); *C40B 40/08* (2013.01)

(58) Field of Classification Search
CPC .......... C07H 21/02; C12N 9/22; C12N 15/64; C12N 2310/20; C12N 2330/51; C12N 15/102; C12N 15/1093; C12N 15/11; C12N 15/70; C40B 50/06; C40B 40/08; C40B 70/00; C12Q 2563/179
See application file for complete search history.

(56) References Cited

U.S. PATENT DOCUMENTS

2017/0369870 A1* 12/2017 Gill .................... C12N 15/1065

FOREIGN PATENT DOCUMENTS

| WO | 2017/176347 A2 | 10/2017 | |
|---|---|---|---|
| WO | 2017/214615 A1 | 12/2017 | |
| WO | WO-2017223538 A1 * | 12/2017 | ........... C12N 15/102 |
| WO | 2018/017419 A1 | 1/2018 | |

OTHER PUBLICATIONS

International Search Report and Written Opinion for Application No. PCT/US2019/016522 mailed Mar. 27, 2019.
International Preliminary Report on Patentability for Application No. PCT/US2019/016522 mailed Aug. 20, 2020.
Guo et al., High-throughput creation and functional profiling of DNA sequence variant libraries using CRISPR-Cas9 in yeast. Nat Biotechnol. Jul. 2018;36(6):540-546. doi: 10.1038/nbt.4147. Epub May 21, 2018.
Sadhu et al., Highly parallel genome variant engineering with CRISPR-Cas9. Nat Genet. Apr. 2018;50(4):510-514. doi: 10.1038/s41588-018-0087-y. Epub Apr. 9, 2018.
PCT/US2019/016522, Mar. 27, 2019, International Search Report and Written Opinion.
PCT/US2019/016522, Aug. 20, 2020, International Preliminary Report on Patentability.

* cited by examiner

*Primary Examiner* — Nelson B Moseley, II
*Assistant Examiner* — Alyssa Rae Stonebraker
(74) *Attorney, Agent, or Firm* — Polsinelli PC

(57) ABSTRACT

Provided herein, in some embodiments, are methods and compositions for gene editing using a trackable gene library, for example, a barcoded and gene edited library.

22 Claims, 13 Drawing Sheets

| colonies counted | cfus/mL | cfus/ug | # edited colonies counted | % editing efficiency |
|---|---|---|---|---|
| 25 | 5,000 | 20,000 | 24 | 96 |
| 0 | 0 | 0 | 0 | 0 |

| colonies counted | cfus/mL | cfus/ug | # edited colonies counted | % editing efficiency |
|---|---|---|---|---|
| 397 | 79,400 | 317,600 | 54 | 13.602015 |
| 160 | 32,000 | 128,000 | 0 | 0 |

| Dose of Metronidazole for Counterselection | Total Colonies Counted on Plate | Correct Edits (Confirmed Barcode sequence) |
|---|---|---|
| 100 ug/mL | 20 | 8/8 |
| 300 ug/mL | 13 | 6/6 |
| 500 ug/mL | 28 | 8/9 |
| 700 ug/mL | 20 | 9/9 |
| Summary Editing Efficiency | | 31/32 (96.9%) |

CONSTRUCTION AND METHODS OF USE OF A BARCODED AND GENE EDITED DNA LIBRARY

RELATED APPLICATIONS

This application is a national stage filing under 35 U.S.C. § 371 of International Patent Application Serial No. PCT/US2019/016522, filed Feb. 4, 2019, which claims the benefit under 35 U.S.C. § 119(e) of U.S. provisional application serial number 62/727,438, filed Sep. 5, 2018, entitled "CONSTRUCTION AND METHODS OF USE OF A BARCODED AND GENE EDITED DNA LIBRARY." This provisional application and the referenced International Patent Application and their respective teachings are incorporated by reference herein in their entireties for all purposes.

GOVERNMENT SUPPORT

This invention was made with government support under grant number DE-SC0008812 awarded by the U.S. Department of Energy, and grant numbers CA075115 and CA085341, awarded by the National Institutes of Health. The government has certain rights in the invention.

BACKGROUND

DNA editing is a relatively low-efficiency event that results in a number of cells lacking the desired DNA edit. Current technologies inadequately differentiate between cells that are unedited and cells that contain a DNA edit. As a result, a large number of unedited cells are propagated in the cell population. The growth dynamics of edited cells are significantly stunted relative to unedited cells, thereby allowing the unedited cells to overtake the cell population. Accordingly, methods and compositions are need for selecting edited cells in a population comprising unedited cells and edited cells, in order to produce a population of edited cells.

SUMMARY

Described herein are methods and compositions for gene editing. In some embodiments, methods and compositions provided herein are useful for producing a population of edited cells. In some embodiments, the population of edited cells comprises a trackable sequence, for example, a barcode. The methods and compositions described herein are useful, in some embodiments, for constructing a barcoded and gene edited library.

Another aspect of the disclosure provides a bacterial cell composition or yeast cell composition comprising a recipient plasmid comprising a selection marker; a barcode landing sequence flanked by a region that is complementary to a portion of a barcode sequence in donor plasmid; and a target nucleic acid sequence that encodes a gene of interest and is flanked by a region that is complementary to a portion of a modified target nucleic acid sequence; and a donor plasmid comprising a selection marker and a counter selection marker, wherein the selection marker and the counter selection marker are not the same; a first guide nucleic acid sequence comprising a region that is complementary to a portion of the barcode landing sequence, wherein the first guide nucleic acid sequence is operably linked to a constitutively active promoter; the barcode sequence; and an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter; a nucleic acid-guided DNA binding protein; and a recombination system.

In some embodiments, a sequence that is flanked by another sequence refers to a sequence having another sequence situated on each end of the sequence (e.g., 5' end and 3' end). In some embodiments, the sequence on each end of a sequence are the same (the same sequence is at the 5' end and at the 3' end). In some embodiments, the sequence on each side of a sequence are not the same (the sequence at the 5' end and the sequence at the 3' end are different). In some embodiments, a sequence that is flanked by a region that is complementary to a portion of another sequence refers to a sequence that has homology arms on either end of the sequence.

In some embodiments, the modified target nucleic acid sequence comprises at least one inserted, deleted, or substituted nucleic acid as compared to the target nucleic acid sequence.

In some embodiments, the nucleic acid-guided DNA binding protein is a Cas9 protein. In some embodiments, the recombination system is selected from the group consisting of a lambda red recombination system, a Cre/Lox recombination system, and an attB/attP recombination system.

In some embodiments, the nucleic acid-guided DNA binding protein; the recombination system; or the nucleic acid-guided DNA binding protein and the recombination system are integrated in a genome of a cell in the population of cells. In some embodiments, the nucleic acid-guided DNA binding protein; the recombination system; or the nucleic acid-guided DNA binding protein and the recombination system are expressed from a plasmid in a cell in the population of cells.

In some embodiments, the selectable marker and counter selectable marker are the same. In some embodiments, the selectable marker and counter selectable marker are not the same. In some embodiments, the selectable marker comprises an antibiotic resistance gene. In some embodiments, the counter selectable marker comprises a nsfl gene. In some embodiments, the selectable marker comprises a SacB gene. In some embodiments, the selectable marker comprises a rpsL gene. In some embodiments, the selectable marker comprises a PheS gene.

Another aspect of the disclosure provides a composition comprising a recipient plasmid comprising a selection marker; a barcode landing sequence flanked by a region that is complementary to a portion of a barcode sequence in donor plasmid; and a target nucleic acid sequence that encodes a gene of interest and is flanked by a region that is complementary to a portion of a modified target nucleic acid sequence; and a donor plasmid comprising a selection marker and a counter selection marker, wherein the selection marker and the counter selection marker are not the same; a first guide nucleic acid sequence comprising a region that is complementary to a portion of the barcode landing sequence, wherein the first guide nucleic acid sequence is operably linked to a constitutively active promoter; the barcode sequence; and an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter.

Another aspect of the disclosure provides a method of gene editing, the method comprising (a) combining a population of cells comprising a nucleic acid-guided DNA binding protein and a recombination system with a recipient plasmid comprising a selection marker; a barcode landing sequence flanked by a region that is complementary to a portion of a barcode sequence; and a target nucleic acid sequence that encodes a gene of interest and is flanked by a region that is complementary to a portion of a modified target nucleic acid sequence; and a donor plasmid comprising a selection marker and a counter selection marker, wherein the selection marker and the counter selection marker are not the same; a first guide nucleic acid sequence comprising a region that is complementary to a portion of the barcode landing sequence, wherein the first guide nucleic acid sequence is operably linked to a constitutively active promoter; the barcode sequence; and an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter, thereby producing a combination; (b) maintaining the combination under conditions under which the first guide nucleic acid sequence and the nucleic acid-guided DNA binding protein create a barcode edit in the barcode landing sequence; (c) selecting for a population of cells comprising the recipient plasmid and the donor plasmid, thereby producing a selected population of cells; (d) maintaining the selected population of cells under conditions under which expression of the second nucleic acid sequence is induced and the expressed second guide nucleic acid sequence and the nucleic acid-guided DNA binding protein create a gene edit in the target nucleic acid sequence; and (e) counter selecting for a population of cells comprising the barcode edit in the barcode landing sequence and the gene edit in the target nucleic acid sequence.

Another aspect of the disclosure provides a bacterial cell composition comprising (a) a recipient plasmid comprising (i) a selection marker; (ii) a barcode landing sequence flanked by a region that is complementary to a portion of a barcode sequence in donor plasmid of (b); and (iii) a target nucleic acid sequence that encodes a gene of interest and is flanked by a region that is complementary to a portion of a modified target nucleic acid sequence; and (b) a donor plasmid comprising (i) a selection marker and a counter selection marker, wherein the selection marker and the counter selection marker are not the same; (ii) a first guide nucleic acid sequence comprising a region that is complementary to a portion of the barcode landing sequence of (a)(ii), wherein the first guide nucleic acid sequence is operably linked to a constitutively active promoter; (iii) the barcode sequence; and (iv) an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter.

In some embodiments, the bacterial cell composition further comprises a nucleic acid-guided DNA binding protein and a recombination system.

DETAILED DESCRIPTION

Figure 1:
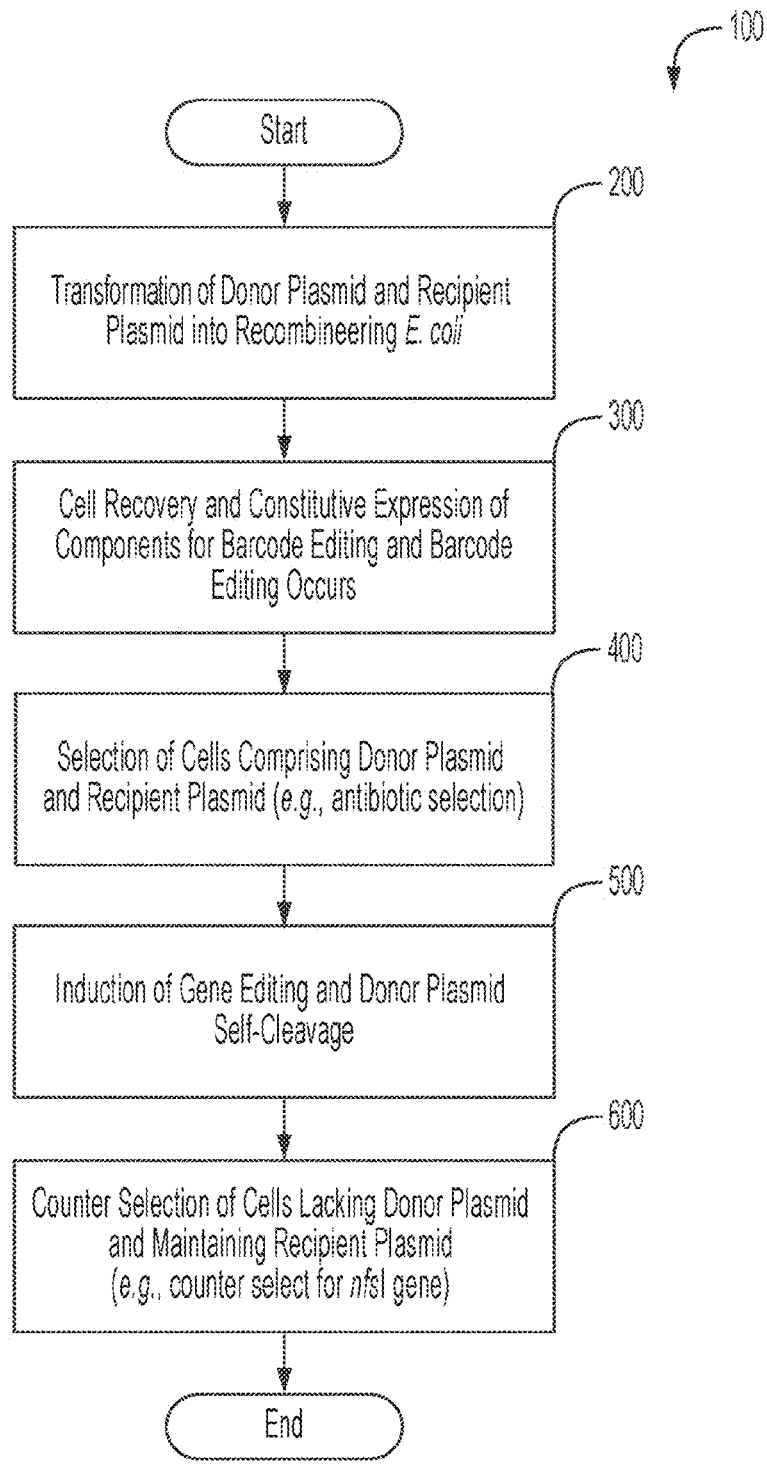
FIG. 1 is a flowchart of an exemplary method for constructing a barcoded and gene edited deoxyribonucleic acid (DNA) library, in accordance with some embodiments of the technology described herein.

Methods and compositions for gene editing are provided herein. The methods and compositions typically involve creating a break in a target sequence that is repaired by Homology-Directed Repair (HDR) using a donor sequence, thereby creating an edited sequence.

Trackable Cassettes

Disclosed herein are methods and compositions for producing a multiplexed and trackable DNA library. In some embodiments, a composition for producing a multiplexed and trackable DNA library comprises a cassette. As used herein, a "cassette" refers to nucleic acids. In some embodiments, the cassette comprises DNA. In some embodiments, the cassette comprises DNA and RNA. In some embodiments, the cassette comprises non-naturally occurring nucleotides or modified nucleotides. In some embodiments, the cassette is single stranded. In some embodiments, the cassette is double stranded.

The terms "nucleic acid," and "polynucleotide," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA.

Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. Alternatively, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

A cassette as described herein may comprise at least one component. Examples of a component include, but are not limited to, a gene of interest (GOI), a selectable marker, a counter selectable marker, a gene editing cassette, a recorder cassette, a trackable sequence, a barcode sequence, a promoter sequence, a guide nucleic acid (e.g., a guide RNA), a riboswitch, a regulatory element, a protospacer adjacent motif (PAM) sequence, a mutant PAM sequence, a synonymous PAM sequence, a homology arm (HA), a primer site, and a linker region.

A cassette as described herein may comprise components in various configurations. In some embodiments, the cassette comprises contiguous components. In some embodiments, the cassette comprises non-contiguous components. In some embodiments, the cassette comprises contiguous components and non-contiguous components.

A cassette as described herein may express a component. In some embodiments, the cassette is configured for constitutive expression of a component. In some embodiments, the cassette is configured for inducible expression of a component. In some embodiments, the component is operably linked to a promoter. In some embodiments, the promoter is a constitutive promoter. In some embodiments, the promoter is an inducible promoter. In some embodiments, the component is linked to an inducible element. In some embodiments, the inducible element is a riboswitch.

A cassette as described herein may be designed for use in a method described herein, e.g., for producing a multiplexed and trackable DNA library. In some embodiments, the cassette is an editing cassette. In some embodiments, the editing cassette comprises a guide nucleic acid (e.g., a gRNA) and an editing sequence. In some embodiments, the editing sequence comprises at least one mutation and at least one homology arm (HA). Exemplary mutations include, but are not limited to, synonymous mutations, a non-synonymous mutations, point mutations, insertions, and deletions.

An editing cassette as provided herein can comprise more than one (at least one) alteration or mutation, which can be of any type, such as an insertion, deletion, addition, substitution, inversion of one or more nucleic acid. In some embodiments, the editing cassette comprises at least 2, at least 3, at least 4, at least 5, at least 6, at least 7, at least 8, at least 9, at least 10 mutations or more mutations. In some embodiments, the editing sequence comprises a mutation in a target sequence. In some embodiments, the editing sequence comprises a mutation in a PAM sequence. In some embodiments, the editing sequence comprises a mutation in a target sequence and a mutation in a PAM sequence. In some embodiments, the mutation in the PAM sequence prevents cleavage by a nucleic acid-guided DNA binding protein.

An editing cassette as provided herein comprises any number of homology arms. In some embodiments, the editing cassette comprises at least 2, at least 3, at least 4, at least 5, at least 6, at least 7, at least 8, at least 9, at least 10 homology arms or more homology arms. In some embodiments, the homology arms of the editing cassette are homologous to a portion of a target sequence. In some embodiments, the homology arms of the editing cassette undergo homologous recombination with a target sequence at a site of a nucleic-acid guided nuclease-mediated double strand break.

The term "target site" or "target sequence" refers to a sequence within a nucleic acid molecule (e.g., a DNA molecule) that is edited as described herein. In some embodiments, the target sequence is a nucleic acid sequence in a genome. In some embodiments, the target sequence is a nucleic acid sequence in a plasmid. In some embodiments, the nucleic acid sequence in the plasmid is a target gene sequence. In some embodiments, the target gene sequence is a selectable marker. In some embodiments, the target gene sequence is a gene of interest.

In some embodiments, the cassette is a recorder cassette. In some embodiments, the recorder cassette comprises a guide nucleic acid (e.g., a gRNA) and an recorder sequence (e.g., a barcode). In some embodiments, the recorder sequence comprises homology arms that undergo homologous recombination with a recorder landing site sequence at a site of a nucleic-acid guided nuclease-mediated double strand break.

In some embodiments, the recorder sequence is a barcode. In some embodiments, the barcode is used to identify a corresponding mutation. In some embodiments, the barcode is a non-naturally occurring sequence that is not found in nature. In some embodiments, the barcode is generated by degenerate oligonucleotide synthesis. In some embodiments, the barcode is rationally designed.

A barcode may be any number of nucleotides in length. In some embodiments, the barcode is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleotides in length.

In some embodiments, the recorder landing site sequence is a barcode landing site sequence. In some embodiments, the barcode landing site sequence is a selectable marker (e.g., nsfI). In some embodiments, the barcode landing site sequence is a selectable marker that is modulated by insertion of the barcode.

A barcode landing site sequence may be any number of nucleotides in length. In some embodiments, the barcode landing site sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length.

Any selectable marker may be used in accordance with methods and compositions described herein. In some embodiments, the selectable marker is an antibiotic resistance gene. In some embodiments the selectable marker is a nitroreductase gene, such as nsfI gene. In some embodiments, the selectable marker is a nsfI gene having a synonymous mutation. In some embodiments, the selectable marker is an auxotrophic marker. In some embodiments, the selectable marker is a fluorescent protein. In some embodiments, the selectable marker comprises a SacB gene. In some embodiments, the selectable marker comprises a rpsL gene. In some embodiments, the selectable marker comprises a PheS gene.

A variety of counter selectable markers may be used in methods and compositions described herein. In some embodiments, the counter selectable marker is an antibiotic resistance gene. In some embodiments the counter selectable marker is a nsfI gene. In some embodiments, the counter selectable marker is a nsfI gene having a synonymous mutation. In some embodiments, the counter selectable marker is an auxotrophic marker. In some embodiments, the counter selectable marker is a fluorescent protein. In some embodiments, the counter selectable marker comprises a SacB gene. In some embodiments, the counter selectable marker comprises a rpsL gene. In some embodiments, the counter selectable marker comprises a PheS gene.

In some embodiments, the cassette comprises a gene editing molecule. In some embodiments, the gene editing molecule induces a strand break. In some embodiments, the gene editing molecule is a nucleic acid-guided DNA binding protein. In some embodiments, the gene editing molecule is Cas9. In some embodiments, the cassette comprises a homologous recombination molecule. In some embodiments, the homologous recombination molecule is lambda red.

A cassette may be comprised within (a component of) a larger nucleic acid sequence, for example, a genome or a plasmid. In some embodiments, the editing cassette is comprised within a larger nucleic acid sequence (e.g., a genome or a plasmid). In some embodiments, the recorder cassette is comprised within a larger nucleic acid sequence (e.g., a genome or a plasmid). In some embodiments, the editing cassette and the recorder cassette are comprised within a larger nucleic acid sequence (e.g., a genome or a plasmid). In some embodiments, the editing cassette and the recorder cassette are covalently linked.

In some embodiments, the cassette is comprised within a donor plasmid (e.g., an editing plasmid) or a recipient plasmid. In some embodiments, the donor plasmid comprises a gene editing cassette, a barcode sequence, a selectable marker, and a guide RNA (gRNA). In some embodiments, the recipient plasmid comprises a gene of interest (GOI), a barcode landing site, and a selectable marker.

Cassettes as described herein may be sequenced with any sequencing methods known in the art. In some embodiments, cassettes are sequenced using short read sequencing technology. In some embodiments, cassettes are sequenced using long read sequencing technology.

A particular advantage of the methods and compositions described herein are editing efficiency. Editing cassettes as described herein can be used for producing gene edits (e.g., target gene edit). Although the methods and compositions described herein may be designed to achieve any desired efficiency, in some embodiments, the efficiency of a gene edit using the editing cassettes described herein is at least 10%. In some embodiments, the efficiency of a gene edit using the editing cassettes described herein is at least 15%, at least 20%, at least 25%, at least 30%, at 40%, at least 50%, at least 60%, at least 70%, at least 80%, at least 90%, at least 95%, at least 99% or at least 100%.

Recorder cassettes as described herein are efficient for producing trackable edits (e.g., barcode edit). In some embodiments, the efficiency of a trackable edit using the recorder cassettes described herein is at least 10%. In some embodiments, the efficiency of a trackable edit using the recorder cassettes described herein is at least 15%, at least 20%, at least 25%, at least 30%, at 40%, at least 50%, at least 60%, at least 70%, at least 80%, at least 90%, at least 95%, at least 99% or at least 100%.

Trackable Cassette Libraries

A plurality of cassettes as described herein can be pooled into a cassette library. In some embodiments, the cassette library comprises at least 2 cassettes. In some embodiments, the cassette library comprises at least 10, at least 100, at least $10^3$, at least $10^4$, at least $10^5$, at least $10^6$, at least $10^7$, at least $10^8$, at least $10^9$, or at least $10^{10}$ cassettes.

In some embodiments, the cassette library comprises at least two editing cassettes. In some embodiments, the cassette library comprises at least two recorder cassettes. In some embodiments, the cassette library comprises at least two donor plasmids. In some embodiments, the cassette library comprises at least two recipient plasmids.

A cassette library may comprise cassettes having common components and/or non-common components. For example, the cassette library comprises at least two cassettes comprising common homology arms and/or non-common barcodes. In some embodiments, the common components are present in a majority of cassettes in the library. In some embodiments, the common components are present in every cassette in the library. In some embodiments, the non-common components are present in minority of cassettes in the library. In some embodiments, the non-common components are present in one cassette in the library.

Cassette libraries may be designed to mutate any number of nucleic acids in a target nucleic acid sequence. In some embodiments, the cassette library comprises a deletion of any number of nucleic acids in a target nucleic acid sequence. In some embodiments, the cassette library comprises an insertion of any number of nucleic acids in a target nucleic acid sequence. In some embodiments, the cassette library comprises a mutation of consecutive nucleic acids in a target nucleic acid sequence. In some embodiments, the cassette library comprises a mutation of non-consecutive nucleic acids in a target nucleic acid sequence.

Cassette libraries may be designed to mutate any number of amino acids in a target protein. In some embodiments, the cassette library comprises a mutation of each amino acid in a target protein. In some embodiments, each amino acid in a target protein is mutated to alanine (e.g., an alanine scanning library). In some embodiments, each amino acid in a target protein is mutated to another amino acid (e.g., a saturation library). In some embodiments, the cassette library comprises a mutation of functionally important amino acids (e.g., a catalytic site mutant). In some embodiments, the cassette library comprises a mutation of consecutive amino acids in a target protein. In some embodiments, the cassette library comprises a mutation of non-consecutive amino acids in a target protein.

Size of a cassette library may vary. In some embodiments, the size of the cassette library depends on number of mutations in a gene of interest. In some embodiments, the size of a full saturation cassette library comprising 20 amino acids at each amino acid position (N) in a protein of interest is N×19. In some embodiments, the size of an alanine scanning cassette library comprising alanine at each amino acid position (N) in a protein of interest is N×1.

A cassette library may be generating using any method known in the art. In some embodiments, the cassette library is generated using custom-synthesized oligonucleotide arrays. In some embodiments, the cassette library is generated by traditional ligation-based cloning. In some embodiments, the cassette library is generated by assembly (e.g., Gibson assembly). In some embodiments, the cassette library is generated by chemical synthesis. In some embodiments, the cassette library is generated by ligation-free cloning.

Programmable Nucleic Acid Cleavage Systems

Disclosed herein are methods and compositions for producing a multiplexed and trackable DNA library using a programmable nucleic acid cleavage system that can be engineered to target to any desired nucleotide sequence within a genome.

A "programmable DNA-binding protein" refers to DNA binding proteins that can be programmed to target to any desired nucleotide sequence within a genome. To program the DNA-binding protein to bind a desired nucleotide sequence, the DNA binding protein may be modified to change its binding specificity, e.g., zinc finger DNA-binding domain, zinc finger nuclease (ZFN), or transcription activator-like effector proteins (TALE). ZFNs are artificial restriction enzymes generated by fusing a zinc finger DNA-binding domain to a DNA-cleavage domain. Zinc finger domains can be engineered to target specific desired DNA sequences and this enables zinc-fingers to bind unique sequences within complex genomes. Transcription activator-like effector nucleases (TALEN) are engineered restriction enzymes that can be engineered to cut specific sequences of DNA. They are made by fusing a TAL effector DNA-binding domain to a nuclease domain (e.g., Fok1). Transcription activator-like effectors (TALEs) can be engineered to bind practically any desired DNA sequence. Methods for programming ZFNs and TALEs are familiar to one skilled in the art.

A "guide nucleotide sequence-programmable DNA-binding protein" refers to a protein, a polypeptide, or a domain that is able to bind DNA, and the binding to its target DNA sequence is mediated by a guide nucleotide sequence. Thus, it is appreciated that the guide nucleotide sequence-programmable DNA-binding protein binds to a guide nucleotide sequence. The "guide nucleotide" may be an RNA or DNA molecule (e.g., a single-stranded DNA or ssDNA molecule) that is complementary to the target sequence and can guide the DNA binding protein to the target sequence. As such, a guide nucleotide sequence-programmable DNA-binding protein may be a RNA-programmable DNA-binding protein (e.g., a Cas9 protein), or an ssDNA-programmable DNA-binding protein (e.g., an Argonaute protein). "Programmable" means the DNA-binding protein may be programmed to bind any DNA sequence that the guide nucleotide targets. Examples of guide nucleotide sequence-programmable DNA-binding proteins include, but are not limited to, Cas9, CasX, CasY, Cpf1, C2c1, C2c2, C2c3, Argonaute, and any other suitable protein described herein, or variants thereof.

In some embodiments, the guide nucleotide sequence exists as a single nucleotide molecule and comprises comprise two domains: (1) a domain that shares homology to a target nucleic acid (e.g., and directs binding of a guide nucleotide sequence-programmable DNA-binding protein to the target); and (2) a domain that binds a guide nucleotide sequence-programmable DNA-binding protein. In some embodiments, domain (2) corresponds to a sequence known as a tracrRNA, and comprises a stem-loop structure. For example, in some embodiments, domain (2) is identical or homologous to a tracrRNA as provided in Jinek et al., *Science* 337:816-821 (2012), which is incorporated herein by reference.

Because the guide nucleotide sequence hybridizes to a target DNA sequence, the guide nucleotide sequence-programmable DNA-binding proteins are able to specifically bind, in principle, to any sequence complementary to the guide nucleotide sequence. Methods of using guide nucleotide sequence-programmable DNA-binding protein, such as Cas9, for site-specific cleavage (e.g., to modify a genome) are known in the art.

As used herein, the term "Cas9" or "Cas9 nuclease" refers to an RNA-guided nuclease comprising a Cas9 protein, a fragment, or a variant thereof. A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek et al., *Science* 337:816-821 (2012), which is incorporated herein by reference.

Cas9 nuclease sequences and structures are well known to those of skill in the art. Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski et al., (2013) RNA Biology 10:5, 726-737; which are incorporated herein by reference.

In some embodiments, Cas9 corresponds to Cas9 from *Streptococcus pyogenes* (NCBI Reference Sequence: NC_002737.2; and Uniport Reference Sequence: Q99ZW2). In some embodiments, Cas9 refers to Cas9 from: *Streptococcus pyogenes* (NCBI Reference Sequence: NC_017053.1), *Corynebacterium ulcerans* (NCBI Refs: NC_015683.1, NC_017317.1), *Corynebacterium diphtheria* (NCBI Refs: NC_016782.1, NC_016786.1), *Spiroplasma syrphidicola* (NCBI Ref: NC_021284.1), *Prevotella intermedia* (NCBI Ref: NC_017861.1), *Spiroplasma taiwanense* (NCBI Ref: NC_021846.1), *Streptococcus iniae* (NCBI Ref:

NC_021314.1), *Belliella baltica* (NCBI Ref: NC_018010.1), *Psychroflexus torquisl* (NCBI Ref: NC_018721.1), *Listeria innocua* (NCBI Ref: NP_472073.1), *Campylobacter jejuni* (NCBI Ref: YP_002344900.1) or *Neisseria meningitidis* (NCBI Ref: YP_002342100.1).

In some embodiments, Cas9 corresponds to a fragment of a Cas9 protein. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example, a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more amino acid changes compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9. In some embodiments, the fragment is at least 100 amino acids in length. In some embodiments, the fragment is at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1050, at least 1100, at least 1150, at least 1200, at least 1250, or at least 1300 amino acids in length.

In some embodiments, the guide nucleotide sequence-programmable DNA-binding protein provided herein is a Cas9 from archaea, for example, CasX or CasY. In some embodiments, the guide nucleotide sequence-programmable DNA-binding protein is CasX or CasY. It should be appreciated that other RNA-guided DNA binding proteins may be used as a guide nucleotide sequence-programmable DNA-binding protein and are within the scope of this disclosure.

Cas9 recognizes a short motif (PAM motif) in the CRISPR repeat sequences in the target DNA sequence. A "PAM motif," or "protospacer adjacent motif," as used herein, refers a DNA sequence immediately following the DNA sequence targeted by the Cas9 nuclease in the CRISPR bacterial adaptive immune system. PAM is a component of the invading virus or plasmid, but is not a component of the bacterial CRISPR locus. Naturally, Cas9 will not successfully bind to or cleave the target DNA sequence if it is not followed by the PAM sequence. PAM is an essential targeting component (not found in the bacterial genome) which distinguishes bacterial self from non-self DNA, thereby preventing the CRISPR locus from being targeted and destroyed by nuclease.

Some aspects of the disclosure provide Cas9 domains that have different PAM specificities. Typically, Cas9 proteins, such as Cas9 from *S. pyogenes* (spCas9), require a canonical NGG PAM sequence to bind a particular nucleic acid region. This may limit the ability to edit desired bases within a genome. Accordingly, in some embodiments, any of the fusion proteins provided herein may contain a Cas9 domain that is capable of binding a nucleotide sequence that does not contain a canonical PAM sequence (e.g., NGG) and has relaxed PAM requirements (PAMless Cas9). PAMless Cas9 exhibits an increased activity on a target sequence that does not include a canonical PAM (e.g., NGG) at its 3'-end as compared to *Streptococcus pyogenes* Cas9, e.g., increased activity by at least 5-fold, at least 10-fold, at least 50-fold, at least 100-fold, at least 500-fold, at least 1,000-fold, at least 5,000-fold, at least 10,000-fold, at least 50,000-fold, at least 100,000-fold, at least 500,000-fold, or at least 1,000,000-fold. Cas9 domains that bind to non-canonical PAM sequences have been described in the art and would be apparent to the skilled artisan.

Thus, the guide nucleotide sequence-programmable DNA-binding protein of the present disclosure may recognize a variety of PAM sequences including, without limitation: NGG, NGAN, NGNG, NGAG, NGCG, NNGRRT, NGRRN, NNNRRT, NNNGATT, NNAGAAW, NAAAC, TTN, TTTN, and YTN, wherein Y is a pyrimidine, and N is any nucleobase.

One example of an RNA-programmable DNA-binding protein that has different PAM specificity is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it utilizes a T-rich protospacer-adjacent motif (TTN, TTTN, or YTN). Moreover, Cpf1 cleaves DNA via a staggered DNA double-stranded break. Out of 16 Cpf1-family proteins, two enzymes from *Acidaminococcus* and *Lachnospiraceae* are shown to have efficient genome-editing activity in human cells.

In some embodiments, the guide nucleotide sequence-programmable DNA binding protein is a Cpf1 protein from an *Acidaminoccous* species (AsCpf1). In some embodiments, the guide nucleotide sequence-programmable DNA binding protein is a Cpf1 protein from a *Lachnospiraceae* species (LbCpf1).

In some embodiments, the guide nucleotide sequence-programmable DNA-binding protein domain of the present disclosure has no requirements for a PAM sequence. One example of such guide nucleotide sequence-programmable DNA-binding protein may be an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at gDNA site. In contrast to Cas9, the NgAgo-gDNA system does not require a protospacer-adjacent motif (PAM). Using a nuclease inactive NgAgo (dNgAgo) can greatly expand the codons that may be targeted.

In some embodiments, the guide nucleotide sequence-programmable DNA-binding protein is a prokaryotic homolog of an Argonaute protein. In some embodiments, the guide nucleotide sequence-programmable DNA-binding protein is a *Marinitoga piezophila* Argunaute (MpAgo)

protein. The CRISPR-associated *Marinitoga piezophila* Argonaute (MpAgo) protein cleaves single-stranded target sequences using 5'-phosphorylated guides. The 5' guides are used by all known Argonautes.

In some embodiments, the guide nucleotide sequence-programmable DNA-binding protein is a single effector of a microbial CRISPR-Cas system. Single effectors of microbial CRISPR-Cas systems include, without limitation, Cas9, Cpf1, C2c1, C2c2, and C2c3. Typically, microbial CRISPR-Cas systems are divided into Class 1 and Class 2 systems. Class 1 systems have multisubunit effector complexes, while Class 2 systems have a single protein effector. Cas9 and Cpf1 are Class 2 effectors. In addition to Cas9 and Cpf1, three distinct Class 2 CRISPR-Cas systems (C2c1, C2c2, and C2c3) have been described. Effectors of two of the systems, C2c1 and C2c3, contain RuvC-like endonuclease domains related to Cpf1. A third system, C2c2 contains an effector with two predicted HEPN RNase domains.

In some embodiments, the guide nucleotide sequence-programmable DNA-binding protein is a C2c1, a C2c2, or a C2c3 protein. In some embodiments, the guide nucleotide sequence-programmable DNA-binding protein is a C2c1 protein. In some embodiments, the guide nucleotide sequence-programmable DNA-binding protein is a C2c2 protein. In some embodiments, the guide nucleotide sequence-programmable DNA-binding protein is a C2c3 protein. In some embodiments, the guide nucleotide sequence-programmable DNA-binding protein comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to a naturally-occurring C2c1, C2c2, or C2c3 protein. In some embodiments, the guide nucleotide sequence-programmable DNA-binding protein is a naturally-occurring C2c1, C2c2, or C2c3 protein. It should be appreciated that C2c1, C2c2, or C2c3 from other bacterial species may also be used in accordance with the present disclosure.

Programmable DNA-binding proteins suitable for use in methods and compositions described herein include wild-type proteins and fusion proteins. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A fusion protein may comprise different domains, for example, a nucleic acid binding domain (e.g., the gRNA binding domain of Cas9 that directs the binding of the protein to a target site), and a nucleic acid cleavage domain or a catalytic domain of a nucleic-acid editing protein (e.g., the RuvC nuclease domain of Cpf1).

In some embodiments, the fusion protein comprises domains from at least two different proteins. In some embodiments, the fusion protein comprises domains from at least 2, at least 3, at least 4, at least 5, at least 6, at least 7, at least 8, at least 9, or at least 10 different proteins.

In some embodiments, the fusion protein comprises domains from at least two different species. In some embodiments, the fusion protein nuclease comprises domains from at least 2, at least 3, at least 4, at least 5, at least 6, at least 7, at least 8, at least 9, or at least 10 different species.

Programmable DNA-binding proteins suitable for use in methods and compositions described herein may be delivered to cells using any method. In some embodiments, nucleic acid molecules (e.g., expression vectors) encoding a programmable DNA-binding protein are delivered into the cell, resulting in expression of the programmable DNA-binding protein in the cell. Nucleic acid molecules encoding a programmable DNA-binding proteins may be delivered into the cell using any known methods in the art, e.g., transfection (e.g., transfection mediated by cationic liposomes), transduction (e.g., via viral infection) and electroporation.

In some embodiments, an isolated programmable DNA-binding protein is delivered. Methods of delivering an isolated protein to a cell are familiar to those skilled in the art. For example, the isolated programmable DNA-binding protein be associated with a supercharged, cell-penetrating protein or peptide, which facilitates its entry into a cell. In some embodiments, the isolated programmable DNA-binding protein may be delivered by a cationic transfection reagent, e.g., the Lipofectamine CRISPRMAX Cas9 Transfection Reagent from Thermofisher Scientific. In some embodiments, the programmable DNA-binding proteins may be delivered separately from the guide nucleic acid.

Guide Nucleic Acids

A guide nucleic acid may be an DNA or RNA molecule that is complementary to the target sequence and can guide the DNA binding protein to the target sequence.

In some embodiments, the guide nucleic acid comprises DNA. In some embodiments, the guide nucleic acid comprises RNA. In some embodiments, the guide nucleic acid comprises RNA encoded by a DNA sequence. In some embodiments, the guide nucleic acid comprises RNA encoded by a DNA sequence of a plasmid. In some embodiments, the guide nucleic acid comprises RNA encoded by a DNA sequence of a construct. In some embodiments, the guide nucleic acid comprises RNA encoded by a DNA sequence of an editing cassette. In some embodiments, the guide nucleic acid comprises DNA and RNA. In some embodiments, the guide nucleic acid comprises non-naturally occurring nucleotides or modified nucleotides.

In some embodiments, the guide nucleic acid comprises a guide RNA sequence (gRNA). A gRNA hybridizes to (complementary to, partially or completely) a target nucleic acid sequence (e.g., a barcode landing site). The gRNA or portion thereof that hybridizes to the target nucleic acid may be between 15-25 nucleotides, 18-22 nucleotides, or 19-21 nucleotides in length. In some embodiments, the gRNA sequence that hybridizes to the target nucleic acid is 15, 16, 17, 18, 19, 20, 21, 22, 23, 24, or 25 nucleotides in length. In some embodiments, the gRNA sequence that hybridizes to the target nucleic acid is between 10-30, or between 15-25, nucleotides in length.

In some embodiments, the gRNA sequence is at least 50%, 55%, 60%, 65%, 70%, 75%, 80%, 85%, 90%, 95%, 96%, 97%, 98%, 99%, or at least 100% complementary to a target nucleic acid. Complementarity of a gRNA sequence with a target polynucleotide sequence may be determined by any method known in the art (see, e.g., U.S. Pat. No. 8,697,359, which is incorporated by reference for its teaching of complementarity of a gRNA sequence with a target polynucleotide sequence). It has been demonstrated that mismatches between a guide sequence and the target nucleic acid near the 3' end of the target nucleic acid may abolish nuclease cleavage activity (see, e.g., Upadhyay, et al. Genes Genome Genetics (2013) 3(12):2233-2238). In some embodiments, the gRNA sequence is at least 50%, 55%, 60%, 65%, 70%, 75%, 80%, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

The "percent identity" of two nucleic acids (e.g., a guide sequence and target nucleic acid) may be determined by any method known in the art. In some embodiments, the percent identity of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, wordlength-12 to obtain guide sequences homologous to a target nucleic acid. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Methods of Use

Aspects of the disclosure relate to using a multiplexed and trackable cassette library for mapping structure-activity relationships (ProSAR) for a gene and/or protein of interest. ProSAR mapping, in some embodiments, identifies individual amino acids for improved activity and/or stability.

In some embodiments, methods and compositions described herein are useful for mapping effects of at least one mutation in at least one protein. In some embodiments, the effect is a change in stability. In some embodiments, the effect is a change in activity. In some embodiments, the effect is a change in production of a product. In some embodiments, the effect is a change in cell growth. In some embodiments, the effect is a change in cell function. In some embodiments, the effect is a change in a response to a chemical.

Host Cells

Methods and compositions described herein may be used in any type of cell in which a nucleic acid-guided nuclease system (e.g., CRISPR) can target and cleave DNA. In some embodiments, a component (e.g., Cas9) of the nucleic acid-guided system (e.g., CRISPR) is integrated into genomic DNA of a cell. In some embodiments, a component (e.g., Cas9) of the nucleic acid-guided system (e.g., CRISPR) is included in a plasmid that can be delivered to a cell.

Methods and compositions described herein, in some embodiments, may be used in any type of cell in which a homologous recombination system can repair DNA via homologous recombination. In some embodiments, a component of the homologous recombination system is integrated into genomic DNA of a cell. In some embodiments, a component of the homologous recombination system is included in a plasmid that can be delivered to a cell. Exemplary homologous recombination systems include, but are not limited to, a lambda red recombination system, a Cre/Lox system, and a attB/attP system.

In some embodiments, methods and compositions described herein are to be used in a cell comprising a nucleic acid-guided nuclease system (e.g., CRISPR) and a recombination system (e.g., lambda red recombineering).

Examples of cells that may be used in accordance with the methods and compositions described herein include, but are not limited to, bacterial cells, fungal cells, yeast cells, plant cells, insect cells, and mammalian cells. In some embodiments, the cell is a bacterial cell. In some embodiments, the bacterial cell is an Escherichia coli (E. coli) cell. In some embodiments, the cell is a fungal cell. In some embodiments, the fungal cell is a yeast cell. In some embodiments, the yeast cell is Saccharomyces cerevisiae (S. cerevisiae).

In some embodiments, the methods and compositions described herein are to be used in an in vitro system or cell-free system in which a nucleic acid-guided nuclease system (e.g., CRISPR) can target and cleave DNA.

Kits

Any of the plasmids and/or cassettes described herein may be provided in a kit. In some embodiments, the kit comprises a donor plasmid as described herein. In some embodiments, the kit comprises a recipient plasmid as described herein. In some embodiments, the kit comprises an editing cassette as described herein. In some embodiments, the kit comprises a recorder cassette as described herein.

In some embodiments, the kit further comprises at least one reagent for performing a method described herein including, but not limited to, methods for producing a multiplexed and trackable nucleic acid library. In some embodiments, the at least one reagent includes, but is not limited to, a ribonucleoside triphosphate, a reaction buffer, and an enzyme (e.g., Cas9).

The kit described herein may include one or more containers housing components for performing the methods described herein and optionally instructions of uses. Any of the kit described herein may further comprise components needed for performing the assay methods. Each component of the kits, where applicable, may be provided in liquid form (e.g., in solution), or in solid form, (e.g., a dry powder). In certain cases, some of the components may be reconstitutable or otherwise processable (e.g., to an active form), for example, by the addition of a suitable solvent or other species (e.g., water or buffer), which may or may not be provided with the kit.

In some embodiments, the kits may optionally include instructions and/or promotion for use of the components provided. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use, or sale of pharmaceuticals or biological products, which can also reflect approval by the agency of manufacture, use or sale for animal administration. As used herein, "promoted" includes all methods of doing business including methods of education, hospital and other clinical instruction, scientific inquiry, drug discovery or development, academic research, pharmaceutical industry activity including pharmaceutical sales, and any advertising or other promotional activity including written, oral and electronic communication of any form, associated with the disclosure. Additionally, the kits may include other components depending on the specific application, as described herein.

The kits may contain any one or more of the components described herein in one or more containers. The components may be prepared sterilely, packaged in a syringe and shipped refrigerated. Alternatively it may be housed in a vial or other container for storage. A second container may have other components prepared sterilely. Alternatively the kits may include the active agents premixed and shipped in a vial, tube, or other container.

The kits may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kits may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kits may also include other components, depending on the specific application, for example, containers, cell media, salts, buffers, reagents, syringes, needles, a fabric, such as gauze, for applying or removing a disinfecting agent, disposable gloves, a support for the agents prior to administration, etc.

EXAMPLES

In order that the invention described herein may be more fully understood, the following examples are set forth. The examples described in this application are offered to illustrate the methods, compositions, and systems provided herein and are not to be construed in any way as limiting their scope.

Example 1: Design and Workflow

FIG. 1 illustrates a non-limiting embodiment of a method for construction of a multiplexed and trackable library (e.g., a barcoded and gene edited DNA library). In some embodiments, the method 100 involves a transformation step 200 in which the donor plasmid and recipient plasmid are taken up by the recombineering E. coli. In some embodiments, the transformation step 200 is followed by a cell recovery step 300 in which components for barcode editing are constitutively expressed, and barcode editing occurs.

In some embodiments, the cell recovery step 300 is followed by a selection step 400 in which recombineering E. coli comprising donor plasmid and recipient plasmid are selected using a selectable marker (e.g., an antibiotic resistance gene). In some embodiments, the selection step 400 is followed by an induction step 500 in which gene editing and donor plasmid self-cleavage occur.

In some embodiments, the induction step 500 is followed by a counter selection step 600 in which recombineering E. coli comprising the recipient plasmid, and lacking the donor plasmid are selected using a counter selectable marker (e.g., counter selection for synonymous nsfI gene).

It should be appreciated that the components used in method 100 are not limiting. For example, method 100 may be performed using components described herein and/or using modified versions of components described herein.

Figure 2:
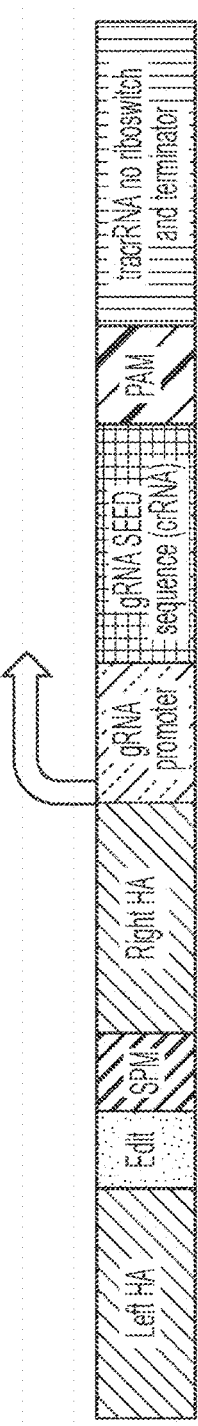
FIG. 2 is a schematic illustrating an example of a gene editing cassette.
Figure 3:
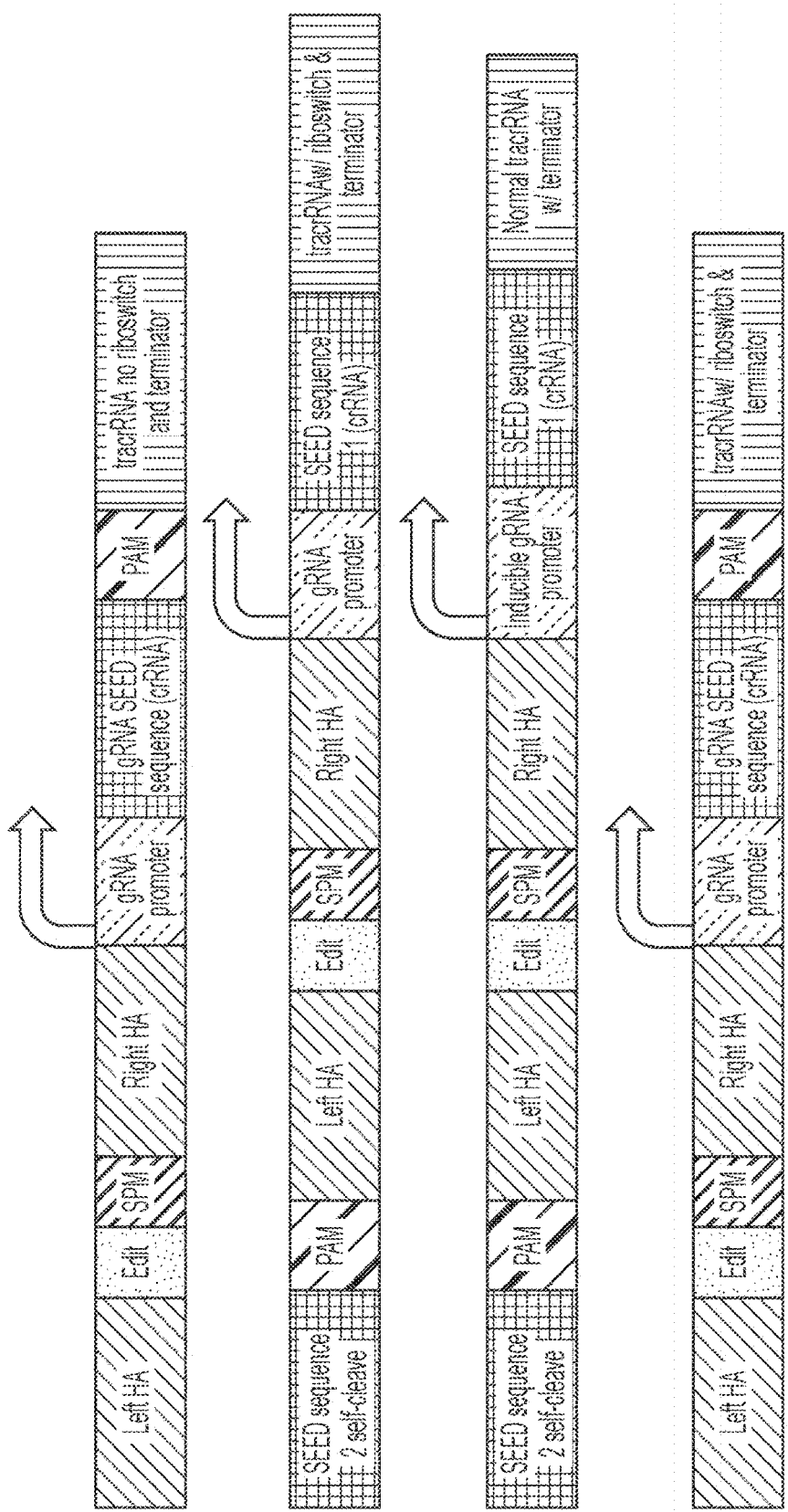
FIG. 3 is a schematic illustrating various configurations of an example of a gene editing cassette.
Figure 4:
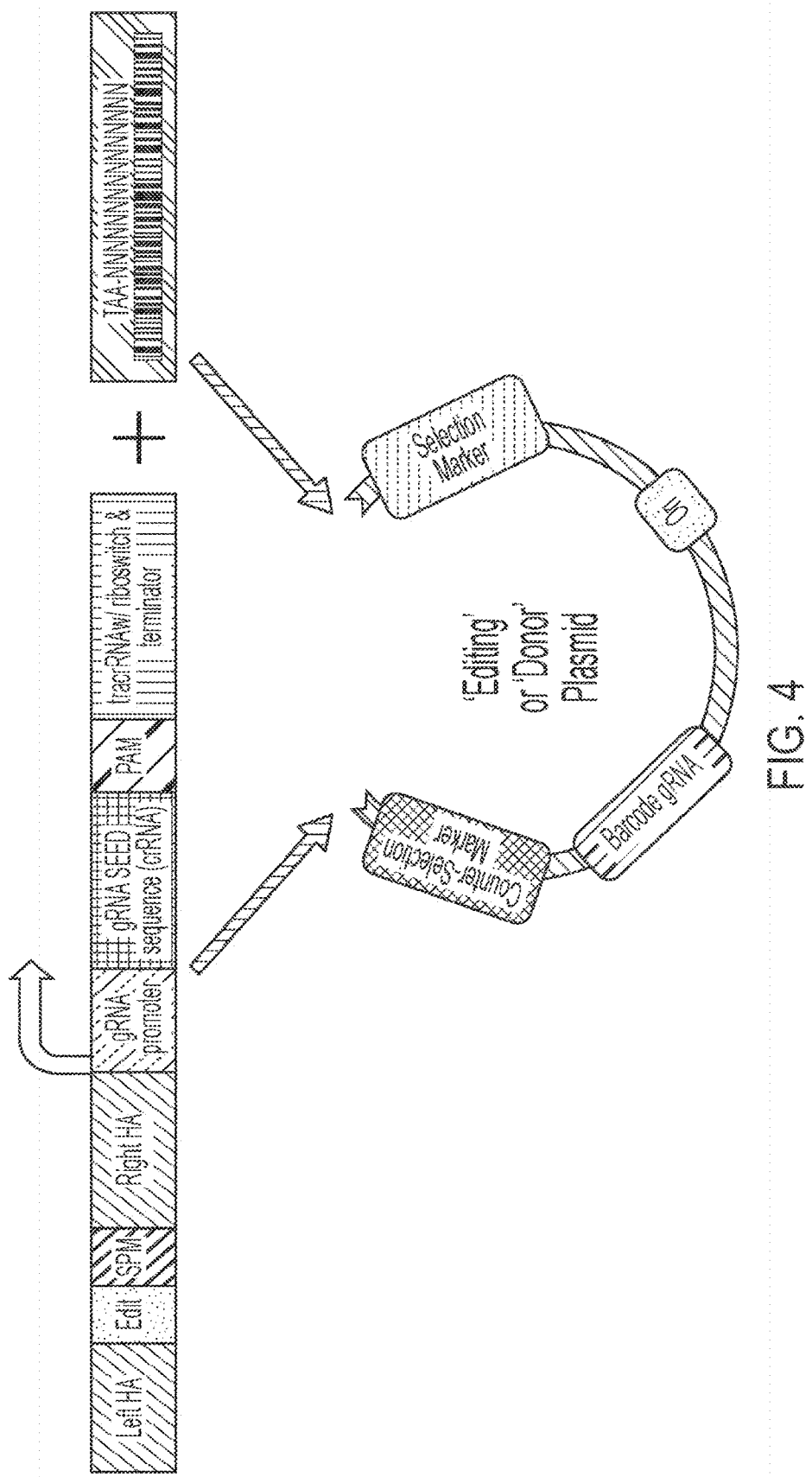
FIG. 4 is a schematic illustrating construction of an example of a donor plasmid.
Figure 5:
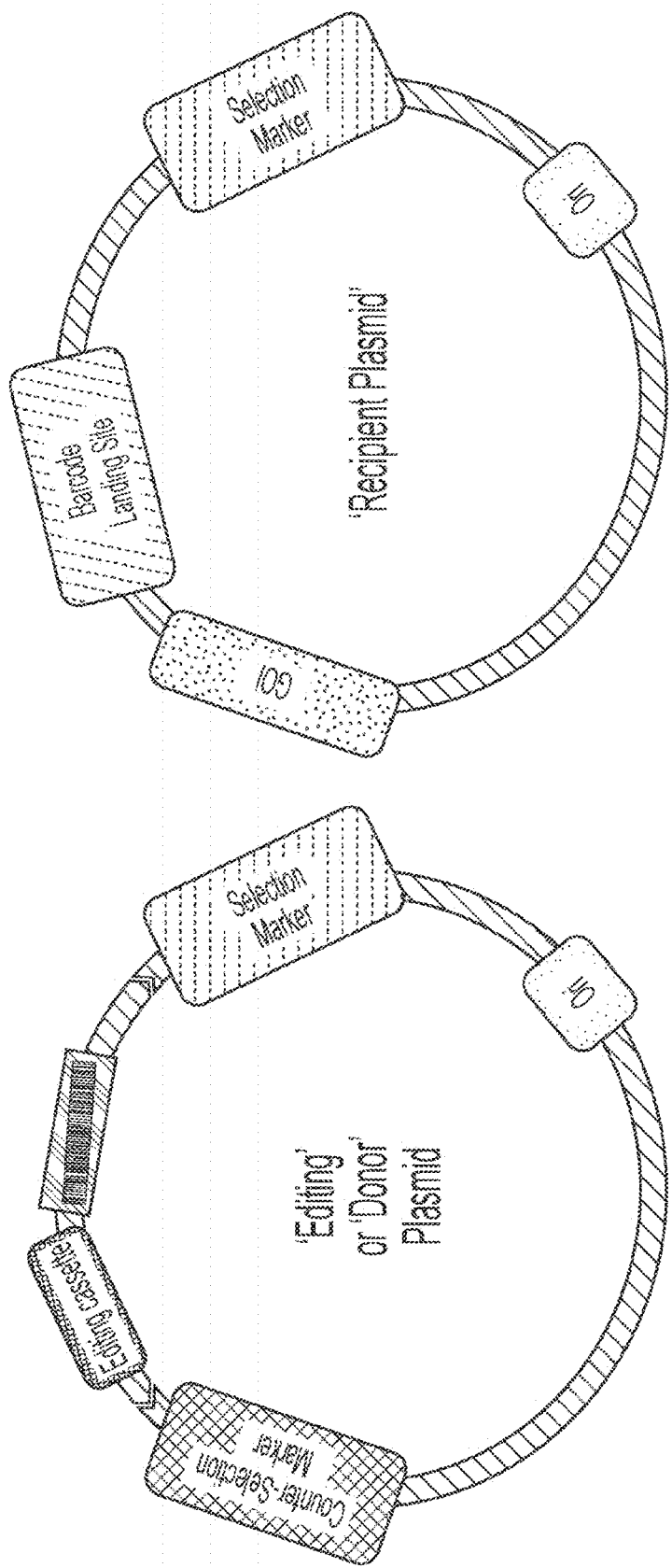
FIG. 5 is a schematic illustrating an example of a donor plasmid and recipient plasmid pair.

Exemplary components for use in the method 100 are shown in FIGS. 2-5. An exemplary gene editing cassette is shown in FIG. 2. Various configurations of an exemplary gene editing cassette are shown in FIG. 3. Insertion of an exemplary gene editing cassette into an exemplary donor plasmid is shown in FIG. 4. An exemplary donor plasmid and recipient plasmid pair are shown in FIG. 5

Example 2: Negative Selection of Cells

Figure 6:
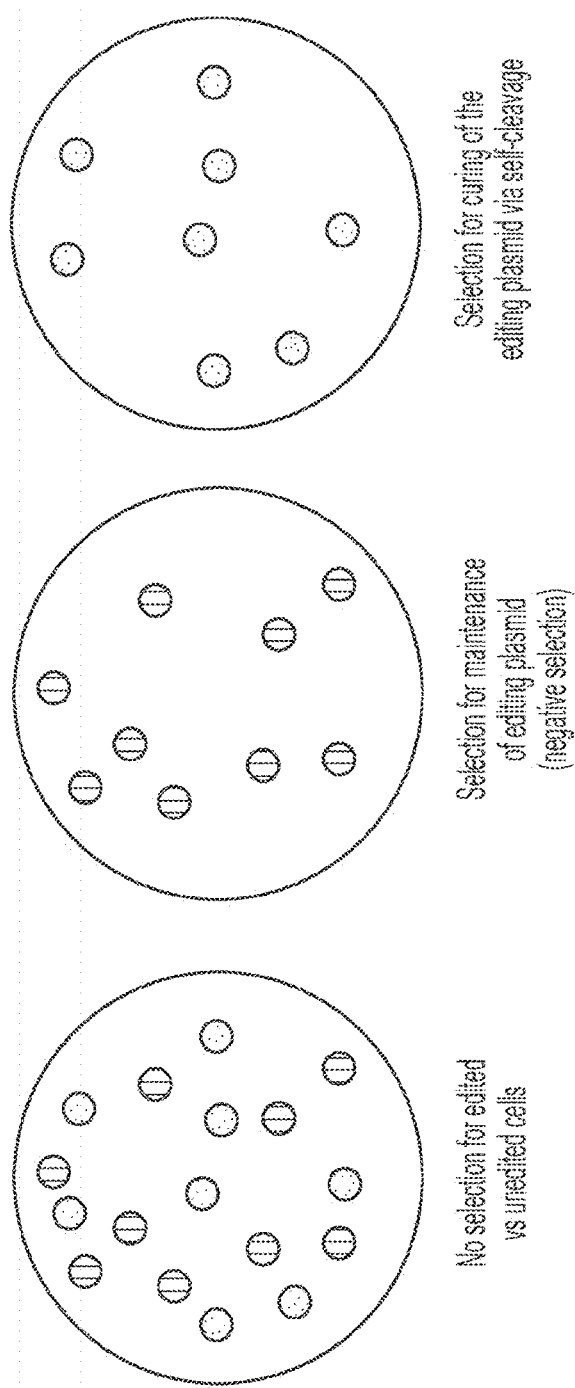
FIG. 6 is a schematic illustrating selection of edited cells and unedited cells.
Figures 7A, 7B:
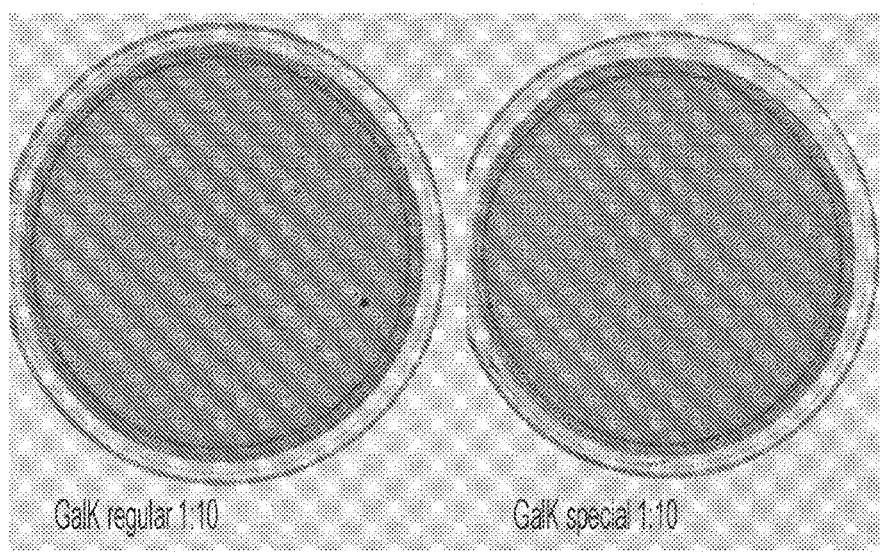
FIG. 7A is a picture of an example of a selection.
FIG. 7B is a chart showing percent editing efficiency of an example of a selection.
Figures 8A, 8B:
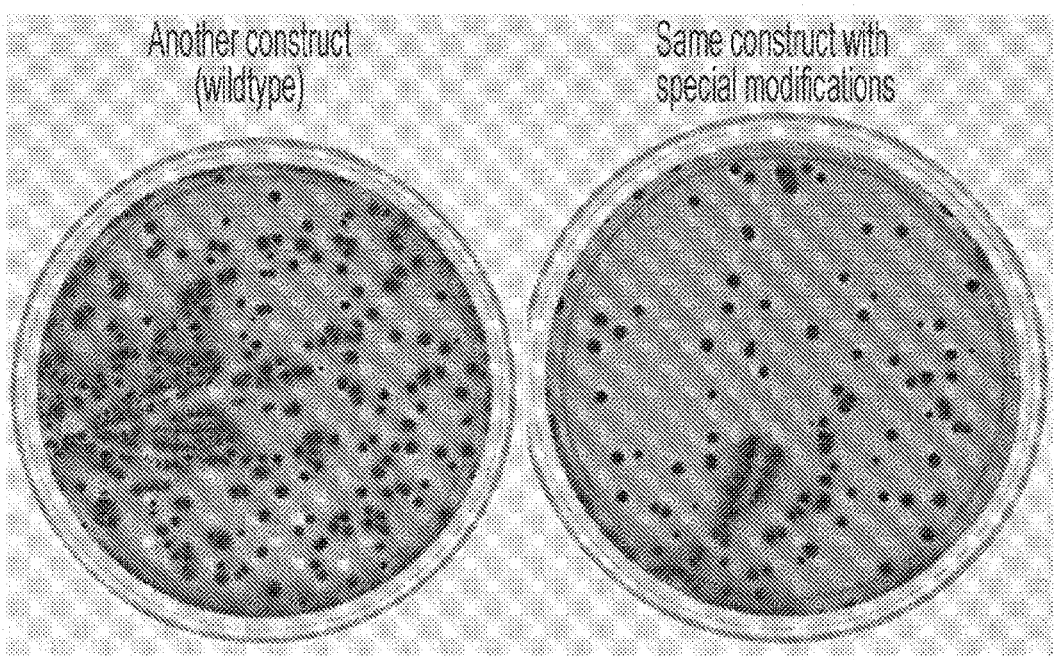
FIG. 8A is a picture of an example of a selection involving a modified editing cassette.
FIG. 8B is a chart showing percent editing efficiency of an example of a selection involving a modified editing cassette.

A schematic illustrating exemplary selection of edited cells and unedited cells is shown in FIG. 6. In some embodiments, galactokinase (GalK) is used as a model protein for methods and compositions described herein. GalK function can be determined from red/white colony screening on MacConkey agar. Thus, mutations in GalK indicative of a gene edit can be determined by red/white colony screening of GalK function. FIGS. 7A-7B shows that negative selection can efficiently remove edited cells. Similar results were obtained using a modified editing cassette, and are shown in FIGS. 8A-8B.

Example 3: Counter Selection of Cells Comprising Edited Recipient Plasmid

Nitroreductase is an enzyme which reduces nitrogen containing compounds. Nitroreductase was found to convert nitro drugs such as metronidazole into their active forms, which is an essential part of their toxicity. Accordingly, nitroreductase can be used as a counter selectable marker.

Figure 9:
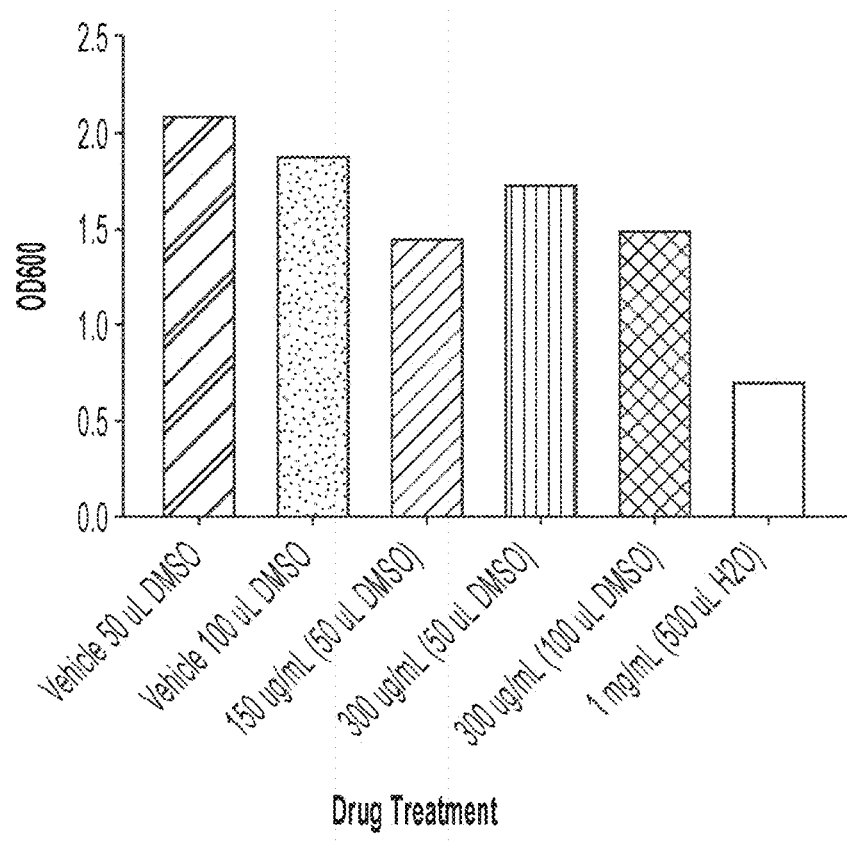
FIG. 9 is a graph showing growth of *E. coli* in the presence of metronidazole.
Figure 10:
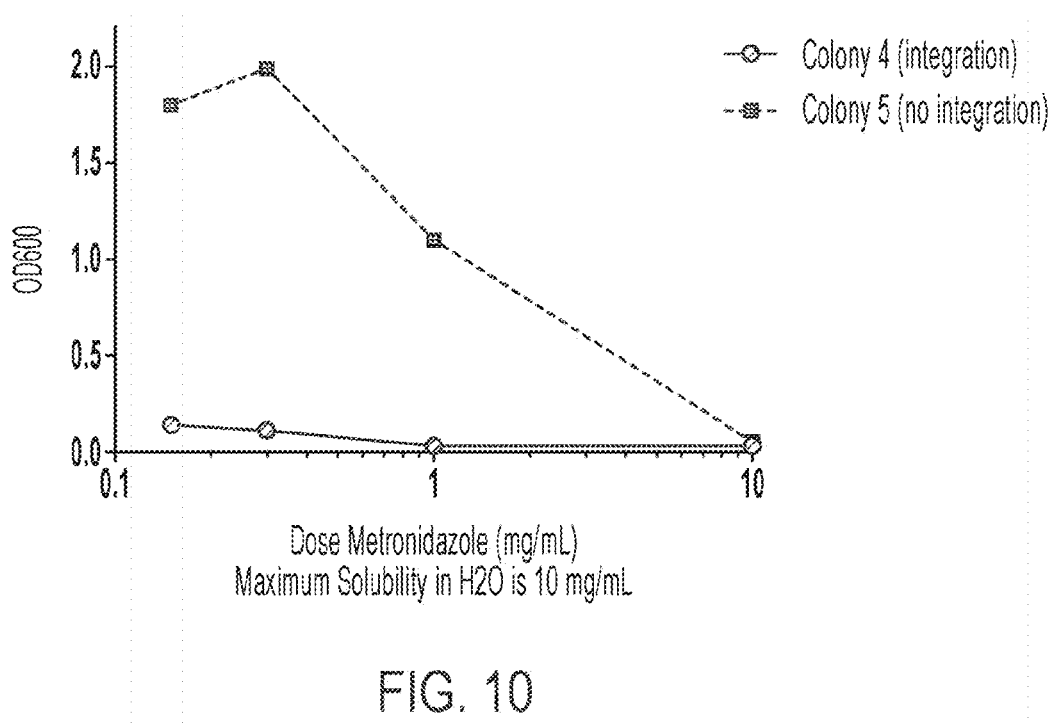
FIG. 10 is a graph showing growth of *E. coli* comprising a nfsI gene in the presence of metronidazole.
Figure 11A:
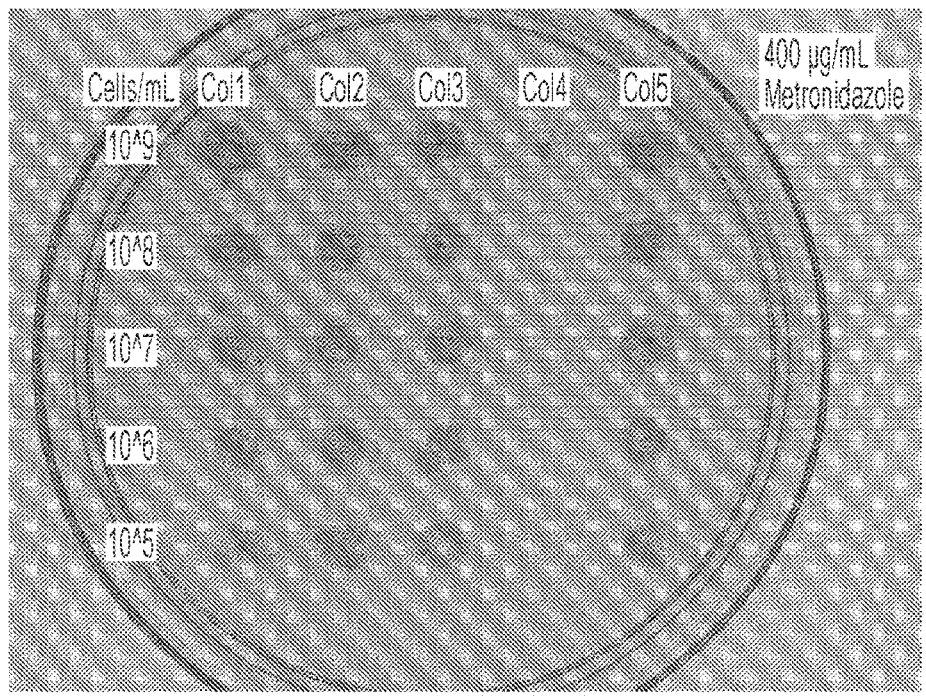
FIG. 11A is a picture of an example of a selection based on nfsI gene inactivation using 400 μg/mL metronidazole.
Figure 11B:
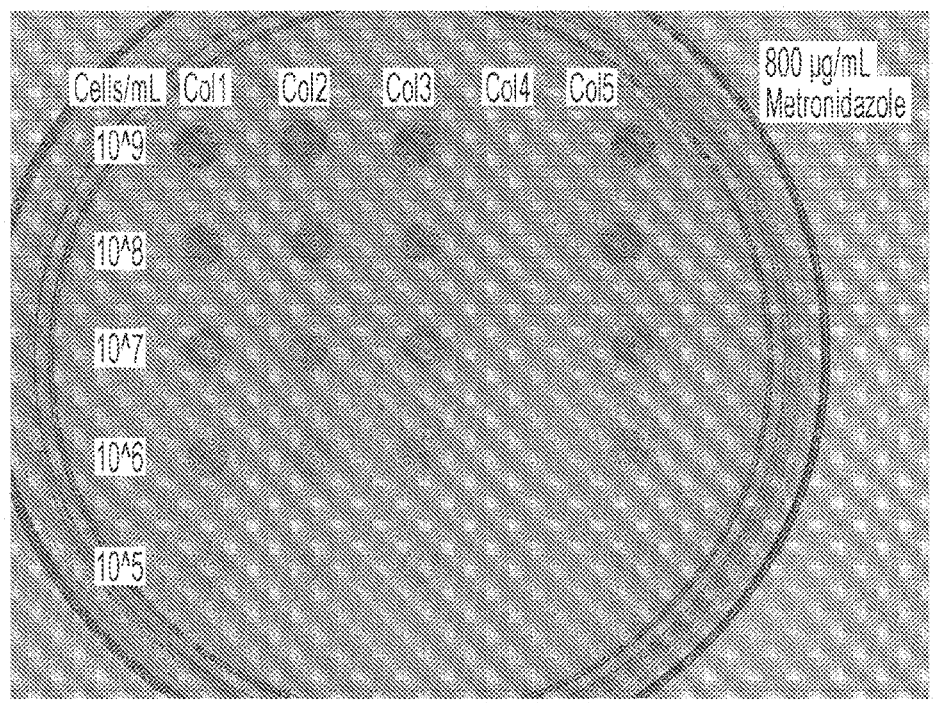
FIG. 11B is a picture of an example of a selection based on nfsI gene inactivation using 800 μg/mL metronidazole.
Figure 11C:
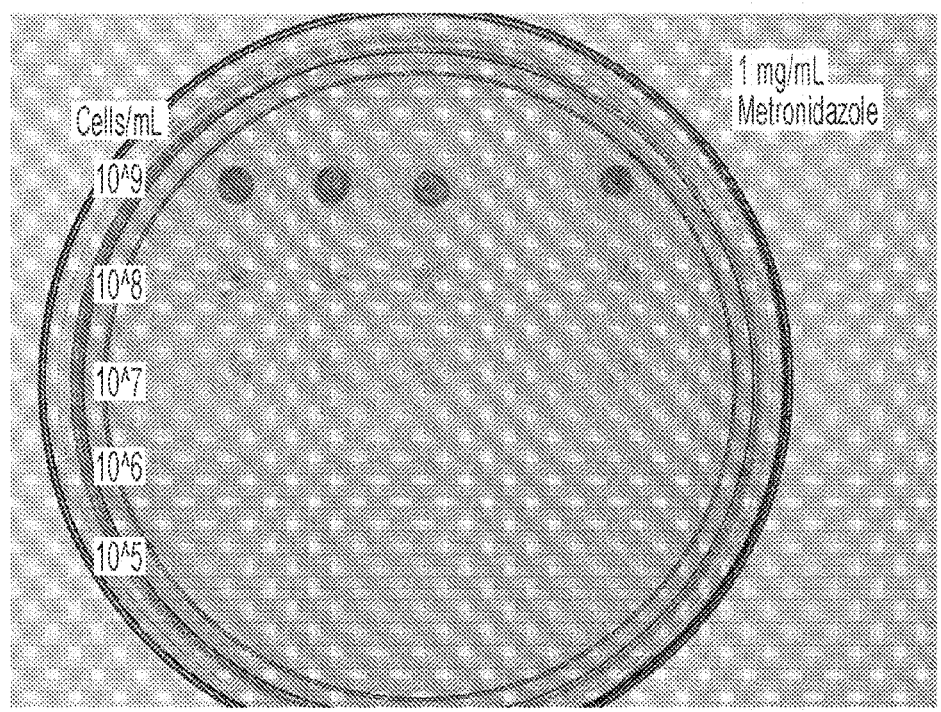
FIG. 11C is a picture of an example of a selection based on nfsI gene inactivation using 1 mg/mL metronidazole.
Figures 12, 13:
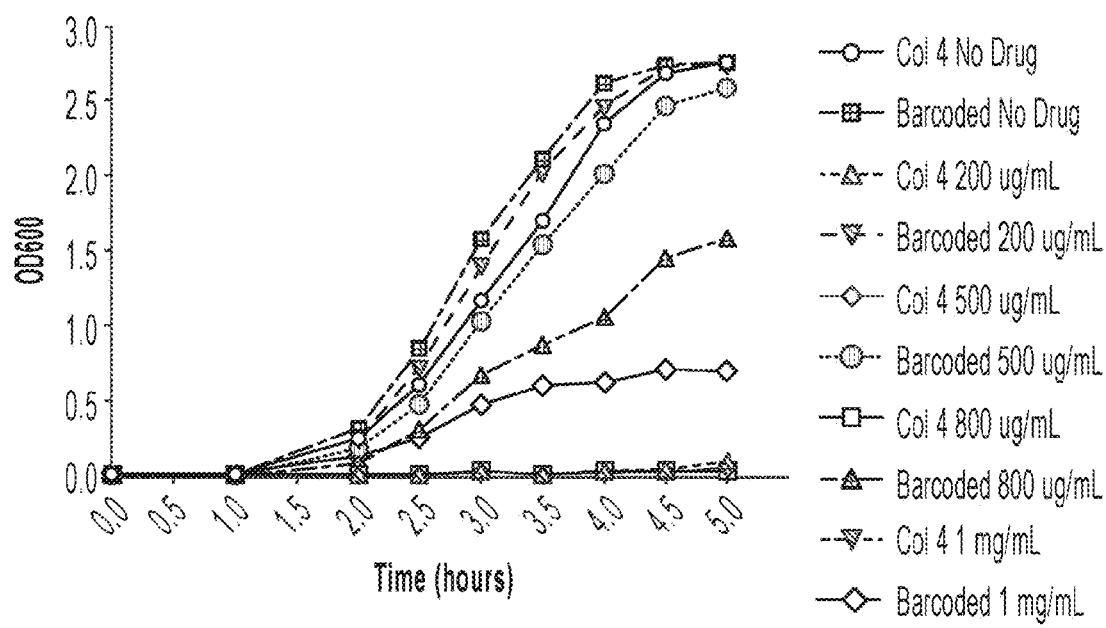
FIG. 12 is a graph showing growth of *E. coli* in the presence of increasing concentrations of metronidazole.
FIG. 13 is a chart showing percent editing efficiency of an example of a counter selection.

Growth of E. coli in the presence of metronidazole was examined. As shown in FIG. 9, low doses of metronidazole did not significantly disrupt E. coli growth as measured by $OD_{600}$. E. coli in which the nsfI gene was integrated displayed significant growth differences in the presence of metronidazole as compared to E. coli lacking the nsfI gene as shown in FIG. 10. E. coli growth on agar plates comprising increasing doses of metronidazole was also examined. As shown in FIGS. 11A-11C, E. coli in which the nfsI gene is inactivated are insensitive to metronidazole. FIGS. 12-13 showed that the efficiency of metronidazole selection improves over time.

EQUIVALENTS AND SCOPE

Those skilled in the art will recognize, or be able to ascertain using no more than routine experimentation, many equivalents of the specific embodiments of the invention described herein.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A bacterial cell composition comprising:
    (a) a recipient plasmid comprising:
        (i) a selection marker;
        (ii) a barcode landing sequence flanked by a region that is complementary to a portion of a barcode sequence in donor plasmid of (b); and
        (iii) a target nucleic acid sequence that encodes a gene of interest and is flanked by a region that is complementary to a portion of a modified target nucleic acid sequence; and
    (b) a donor plasmid comprising:
        (i) a selection marker and a counter selection marker, wherein the selection marker and the counter selection marker are not the same;
        (ii) a first guide nucleic acid sequence comprising a region that is complementary to a portion of the barcode landing sequence of (a)(ii), wherein the first guide nucleic acid sequence is operably linked to a constitutively active promoter;
        (iii) the barcode sequence; and
        (iv) an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter;
    (c) a nucleic acid-guided DNA binding protein; and
    (d) a recombination system.

2. The bacterial cell composition of claim 1, wherein the modified target nucleic acid sequence comprises at least one inserted, deleted, or substituted nucleic acid as compared to the target nucleic acid sequence.

3. The bacterial cell composition of claim 1, wherein the nucleic acid-guided DNA binding protein is a Cas9 protein.

4. The bacterial cell composition of claim 1, wherein the recombination system is selected from the group consisting of a lambda red recombination system, a Cre/Lox recombination system, and an attB/attP recombination system.

5. The bacterial cell composition of claim 1, wherein the nucleic acid -guided DNA binding protein; the recombination system; or the nucleic acid-guided DNA binding protein and the recombination system are integrated in a genome of a cell.

6. The bacterial cell composition of claim 1, wherein the nucleic acid-guided DNA binding protein; the recombination system; or the nucleic acid-guided DNA binding protein and the recombination system are expressed from a plasmid in a cell.

7. The bacterial cell composition of claim 1, wherein at least one of the selection markers in (a) and (b) comprises an antibiotic resistance gene.

8. The bacterial cell composition of claim 1, wherein the counter selection marker comprises a nsfl gene.

9. A composition comprising:
    (a) a recipient plasmid comprising:
        (i) a selection marker;
        (ii) a barcode landing sequence flanked by a region that is complementary to a portion of a barcode sequence; and
        iii) a target nucleic acid sequence that encodes a gene of interest and is flanked by a region that is complementary to a portion of a modified target nucleic acid sequence; and
    (b) a donor plasmid comprising:
        (i) a selection marker and a counter selection marker wherein the selection marker and the counter selection marker are not the same;
        (ii) a first guide nucleic acid sequence comprising a region that is complementary to a portion of the barcode landing sequence, wherein the first guide nucleic acid sequence is operably linked to a constitutively active promoter;
        (iii) the barcode sequence; and
        (iv) an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter.

10. The composition of claim 9, wherein the modified target nucleic acid sequence comprises at least one inserted, deleted, or substituted nucleic acid as compared to the target nucleic acid sequence.

11. The composition of claim 9, wherein at least one of the selection markers in (a) and (b) comprises an antibiotic resistance gene.

12. The bacterial cell composition of claim 1, wherein the counter selection marker comprises a nsfl gene.

13. A method of gene editing, the method comprising:
combining a population of cells comprising a nucleic acid-guided DNA binding protein and a recombination system with:
(a) a recipient plasmid comprising:
  (i) a selection marker;
  (ii) a barcode landing sequence flanked by a region that is complementary to a portion of a barcode sequence; and
  (iii) a target nucleic acid sequence that encodes a gene of interest and is flanked by a region that is complementary to a portion of a modified target nucleic acid sequence; and
(b) a donor plasmid comprising:
  (i) a selection marker and a counter selection marker, wherein the selection marker and the counter selection marker are not the same;
  (ii) a first guide nucleic acid sequence comprising a region that is complementary to a portion of the barcode landing sequence, wherein the first guide nucleic acid sequence is operably linked to a constitutively active promoter;
  (iii) the barcode sequence; and
  (iv) an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter, thereby producing a combination;
maintaining the combination under conditions under which the first guide nucleic acid sequence and the nucleic acid-guided DNA binding protein create a barcode edit in the barcode landing sequence;
selecting for a population of cells comprising the recipient plasmid and the donor plasmid, thereby producing a selected population of cells;
maintaining the selected population of cells under conditions under which expression of the second nucleic acid sequence is induced and the expressed second guide nucleic acid sequence and the nucleic acid-guided DNA binding protein create a gene edit in the target nucleic acid sequence; and
counter selecting for a population of cells comprising the barcode edit in the barcode landing sequence and the gene edit in the target nucleic acid sequence.

14. The method of claim 13, wherein the modified target nucleic acid sequence comprises at least one inserted, deleted, or substituted nucleic acid as compared to the target nucleic acid sequence.

15. The method of claim 13, wherein the nucleic acid-guided DNA binding protein is a Cas9 protein.

16. The method of claim 13, wherein the recombination system is selected from the group consisting of a lambda red recombination system, a Cre/Lox recombination system, and an attB/attP recombination system.

17. The method of claim 13, wherein the nucleic acid-guided DNA binding protein;
the recombination system; or the nucleic acid-guided DNA binding protein and the recombination system are integrated in a genome of a cell.

18. The method of claim 13, wherein the nucleic acid-guided DNA binding protein;
the recombination system; or the nucleic acid-guided DNA binding protein and the recombination system are expressed from a plasmid in a cell.

19. The composition of claim 13, wherein at least one of the selection markers in (a) and (b) comprises an antibiotic resistance gene.

20. The bacterial cell composition of claim 1, wherein the counter selection marker comprises a nsfl gene.

21. A bacterial cell composition comprising:
(a) a recipient plasmid comprising:
  (i) a selection marker;
  (ii) a barcode landing sequence flanked by a region that is complementary to a portion of a barcode sequence in donor plasmid of (b); and
  (iii) a target nucleic acid sequence that encodes a gene of interest and is flanked by a region that is complementary to a portion of a modified target nucleic acid sequence; and
(b) a donor plasmid comprising:
  i) a selection marker and a counter selection marker, wherein the selection marker and the counter selection marker are not the same;
  (ii) a first guide nucleic acid sequence comprising a region that is complementary to a portion of the barcode landing sequence of (aii), wherein the first guide nucleic acid sequence is operably linked to a constitutively active promoter;
  (iii) the barcode sequence; and
  (iv) an editing cassette comprising the modified target nucleic acid sequence linked to a mutated protospacer adjacent motif (mutated PAM) and a second guide nucleic acid sequence comprising a region that is complementary to a portion of the editing cassette, wherein the second guide nucleic acid sequence is operably linked to an inducible promoter.

22. The bacterial cell composition of claim 21, further comprising a nucleic acid-guided DNA binding protein and a recombination system.

* * * * *